(12) United States Patent
Smith

(10) Patent No.: US 11,865,681 B2
(45) Date of Patent: Jan. 9, 2024

(54) STERILE LINE CLIP SEPARATION TOOL

(71) Applicant: Merck Sharp & Dohme LLC, Rahway, NJ (US)

(72) Inventor: Derrick Matthew Smith, Newtown Square, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 218 days.

(21) Appl. No.: 16/934,560

(22) Filed: Jul. 21, 2020

(65) Prior Publication Data
US 2022/0024008 A1    Jan. 27, 2022

(51) Int. Cl.

| | | |
|---|---|---|
| B25B 27/14 | (2006.01) | |
| F16L 3/00 | (2006.01) | |
| B33Y 80/00 | (2015.01) | |
| B25G 1/10 | (2006.01) | |
| B25B 27/20 | (2006.01) | |
| B33Y 50/02 | (2015.01) | |
| A61B 17/122 | (2006.01) | |
| G06F 113/10 | (2020.01) | |

(52) U.S. Cl.
CPC ............ *B25B 27/14* (2013.01); *A61B 17/122* (2013.01); *B25B 27/146* (2013.01); *B33Y 50/02* (2014.12); *B33Y 80/00* (2014.12); *F16L 3/00* (2013.01); *B25B 27/205* (2013.01); *B25G 1/102* (2013.01); *G06F 2113/10* (2020.01)

(58) Field of Classification Search
CPC ....... B25B 27/146; B25B 27/205; B25B 7/06; B25B 7/12; B25B 13/488; A61M 39/28; A61M 39/284; A61M 39/285; A61M 39/286; A61M 39/287; A61B 17/122; A61B 17/128; B65B 13/345; F16K 7/06–068; B29C 57/10
USPC ....... 81/302, 485, 9.3, 426.5, 418, 426, 304, 81/305, 306, 307, 423, 421, 13, 3.8, 3.7, 81/311, 312; 29/225, 270, 243.56, 268, 29/238; D8/52, 54, 58
See application file for complete search history.

(56) References Cited

U.S. PATENT DOCUMENTS

| | | | | |
|---|---|---|---|---|
| 197,717 A | * | 12/1877 | Caldwell | B25B 25/005 140/121 |
| 717,526 A | * | 1/1903 | Barney | B25B 27/205 81/424.5 |
| 2,523,936 A | * | 9/1950 | Axelsen | H02G 1/1212 81/9.42 |

(Continued)

*Primary Examiner* — Tom Rodgers
*Assistant Examiner* — Jacob Adam Montgomery
(74) *Attorney, Agent, or Firm* — Fenwick & West LLP

(57) ABSTRACT

A system and a method are disclosed for disconnecting clips. A clip separation tool includes two arms, the arms having jaws to receive connected clips at a distal end of the arms and handle portions on a proximal end for a user to engage the tool with his hand. A pivot mechanism is coupled to the arms, where, responsive to a force applied to the handle portions, the arms rotate relative to each other around the pivot mechanism such that the distal ends of the arms pivot away from one another and the proximal ends of the arms pivot towards one another. A spring biases the arms to rotate to an equilibrium position that is attained automatically under spring loading once the proximal ends of the arms are relieved of loading. The clip separation tool disconnects connected clips as the force causes the arms to rotate around the pivot mechanism.

10 Claims, 5 Drawing Sheets

(56) References Cited

U.S. PATENT DOCUMENTS

| | | | | |
|---|---|---|---|---|
| 3,677,129 | A * | 7/1972 | Lyon | G10D 7/10 |
| | | | | 984/143 |
| 4,367,577 | A * | 1/1983 | Muff | B25B 27/02 |
| | | | | 29/234 |
| 4,475,418 | A * | 10/1984 | Tani | H02G 1/1212 |
| | | | | 81/9.41 |
| 4,571,808 | A * | 2/1986 | King | B25B 27/10 |
| | | | | 29/268 |
| 4,875,394 | A * | 10/1989 | Crudgington, Jr. | B67B 7/066 |
| | | | | 81/3.36 |
| 4,951,529 | A * | 8/1990 | Laurencot | H02G 1/1212 |
| | | | | 81/9.43 |
| 5,797,922 | A * | 8/1998 | Hessel | A61B 17/128 |
| | | | | 606/120 |
| 5,884,540 | A * | 3/1999 | Mo | B25B 7/04 |
| | | | | 81/426 |
| 6,314,629 | B1 * | 11/2001 | Showalter, Sr | B25B 27/10 |
| | | | | 7/125 |
| 7,497,150 | B1 * | 3/2009 | Huang | B25B 7/18 |
| | | | | 81/302 |
| 8,307,745 | B2 * | 11/2012 | Christensen, III | B25B 7/12 |
| | | | | 81/485 |
| 8,910,918 | B2 | 12/2014 | Gay et al. | |
| 8,978,226 | B2 * | 3/2015 | Kady | B25B 5/068 |
| | | | | 7/125 |
| 9,527,195 | B1 * | 12/2016 | Deane | B25B 27/10 |
| 2008/0277635 | A1 * | 11/2008 | Clark | B25B 25/00 |
| | | | | 254/248 |
| 2017/0232595 | A1 * | 8/2017 | Liu | B25B 7/12 |
| | | | | 81/302 |

\* cited by examiner

STERILE LINE CLIP SEPARATION TOOL

TECHNICAL FIELD

The disclosure generally relates to a tool for disconnecting clips and in particular, to a tool for disconnecting clips in an industrial environment.

BACKGROUND

To prevent the content within tubing from escaping while severing the tubing, sterile line clips are connected around the tubing and sever the tubing at the point of connection. In this way, sterility is maintained in the tubing on either side of the split and the severing does not contaminate the environment. However, the sterile line clips can be manufactured with particular tolerances to meet the requirements of a cleanroom at the expense of ease-of-use. In particular, the clips can be difficult and time-consuming to separate once connected. Separating the clips by hand has ergonomic implications because of the force, soft tissue compression, and impact stress induced throughout the process. Furthermore, if significant force is applied to separate the two sides of a clip, this can lead to spills when separation does occur, compromising the sterility of the environment.

SUMMARY

A clip separation tool is used to disconnect clips such as sterile line clips used in cleanrooms. The clip separation tool enables a user to disconnect clips while reducing both the need for over-exertion and the time required to disconnect the clips relative to conventional approaches. The tool may be operated using one hand, leaving the user's other hand free for other tasks, such as securing the line being unclipped.

In one embodiment, the clip separation tool includes first and second arms, a pivot mechanism, and a spring. Each arm of the two arms includes a distal end having two jaws and a proximal end, opposite the distal end, having a handle portion. The pivot mechanism is coupled to the arms. Responsive to a force applied to the handle portions of the arms, the arms may rotate relative to each other around the pivot mechanism in a rotational plane such that the distal ends of the arms pivot away from one another and the proximal ends of the arms pivot towards one another. The spring biases the arms to rotate to an equilibrium position, which is attained automatically under spring loading once the proximal ends of the arms are relieved of loading. In the equilibrium position, the pairs of jaws are substantially aligned such that the top jaws of each arm are within one plane and the bottom jaws of each arm are within another, allowing a connected pair of clips to fit within the jaws.

The pivot mechanism may include an axle, around which the arms are configured to rotate, and fastening elements configured to restrict the movement of the arms to movement within the rotational plane. The proximal ends of the arms may overlap with one another such that the width of the distal end of the tool is larger than the width of the proximal end of the tool. The pair of jaws of each arm includes a top jaw and a bottom jaw, where each top jaw includes a top surface configured to engage with a top surface of a tubing attachment and each bottom jaw includes a bottom surface configured to engage with a bottom surface of a tubing attachment. The pairs of jaws of each arm cooperate to disconnect tubing attachments that are connected to one another responsive to a force being applied to the handle portions of the arms.

The jaws may be adjustable to engage with different sizes of tubing attachments. The tool may be configured for use in a classified environment such as an International Organization for Standardization 7 (ISO 7) environment. The tool may be composed of at least one of nylon, reinforced nylon, carbon fiber, metal, glass fiber, Somos Next®, etc. In some embodiments, outer surfaces of the proximal ends of the arms include respective protrusions structured to align with a curvature of a finger pad. The clip separation tool may be fabricated using a three-dimensional (3D) printer or any other suitable method of additive manufacturing.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

DETAILED DESCRIPTION

Figure 1:
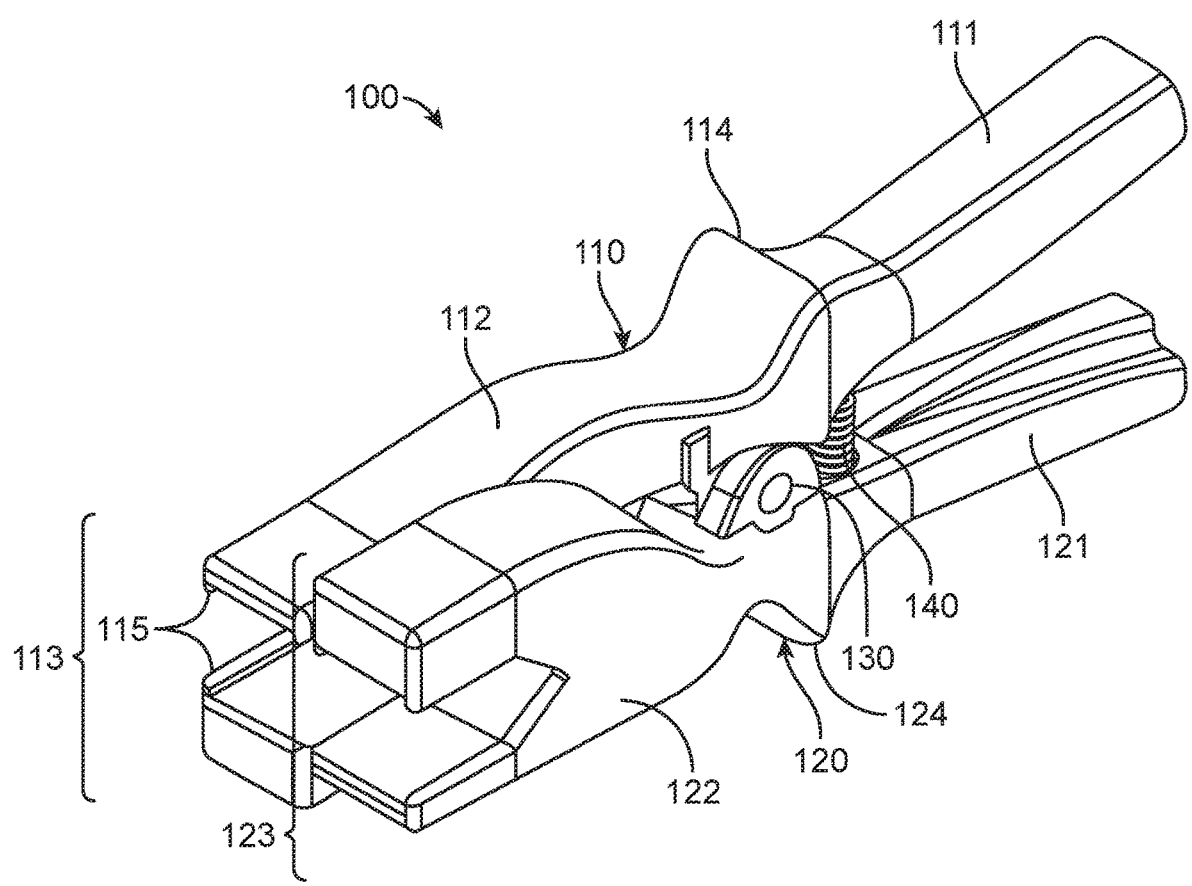
FIG. 1 is a perspective view at a distal end of a clip separation tool, according to one example embodiment.

The Figures (FIGS.) and the following description describe certain embodiments by way of illustration only. One skilled in the art will readily recognize from the following description that alternative embodiments of the structures and methods may be employed without departing from the principles described. Wherever practicable, similar or like reference numerals identify similar or identical structural elements or identify similar or like functionality. For clarity within the figures, reference numerals may refer to less than all instantiations of the feature referenced. For example, the raised edges 115 are referenced for the first arm 110 of the clip separation tool 100, but not for the raised edges depicted in the second arm 120 to maintain clarity within the figures.

Throughout the following description, the term "proximal" refers to the end of the apparatus which is closer to the user when being used as intended and described, and the term "distal" refers to the end of the apparatus which is further away from the user when being used as intended and described. The following description relates to embodiments of the apparatus for use with a "clip" that is an aseptic disconnector for disconnecting tubing in non-classified and classified (e.g., ISO 7 classified) environments. The terms "clip" and "tubing attachment" are used interchangeably herein. In other embodiments, the apparatus may be used with other types of clips.

Clip Separation Tool Structure

FIGS. 1-5 show the structure of an embodiment of a clip separation tool 100 through various views. In the embodiment shown, the clip separation tool 100 includes arms 110 and 120, a pivot mechanism 130, and a spring 140. The arm 110 includes a proximal end 111 and a distal end 112 opposite from one another. Similarly, the arm 120 includes a proximal end 121 and a distal end 122. The proximal ends 111 and 121 each include respective handle portions. In some embodiments, the outer surface of at least one of the proximal ends 111 and 121 includes a protrusion 114, 124 structured to align with a curvature of a finger pad (e.g., a thumb pad). The distal ends 112 and 122 each include respective pairs of jaws 113 and 123. The arms 110 and 120 may be the same structure such that the tool is created from attaching an arm to a rotated copy of itself (e.g., rotated by 180 degrees).

Figure 2:
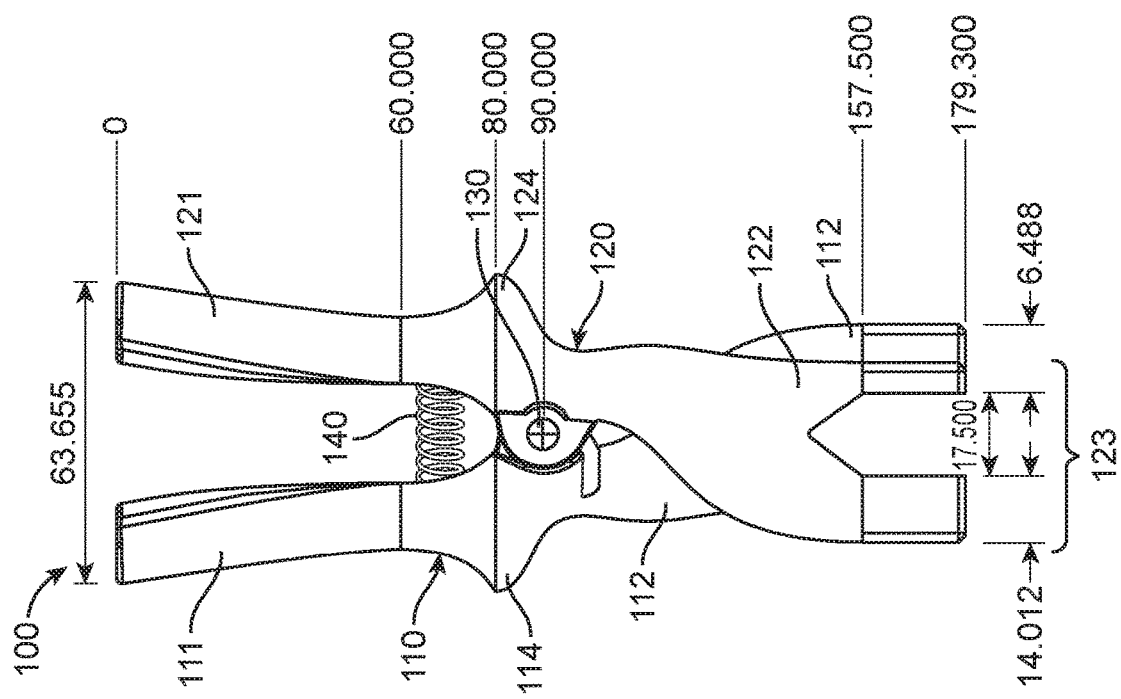
FIG. 2 is a side view of the clip separation tool of FIG. 1, according to one example embodiment.

The pivot mechanism 130 couples the arm 110 to the arm 120. In some embodiments, the pivot mechanism 130 limits the position of arms 110 and 120 such that they may rotate relative to each other around the pivot mechanism 130. The pivot mechanism 130 may include an axle and a plurality of fastening elements. The plurality of fastening elements may connect the axle to the pivot mechanism 130. For example, the pivot mechanism 130 may include a double-ended threaded stud and a set of nuts, a sex bolt, or any suitable mechanism for fastening the arms 110 and 120 in a position that allows them to rotate relative to one another. In some embodiments, the pivot mechanism 130 is coupled to the arms 110 and 120 at locations at the center of the inner surface of each arm 110 and 120. The pivot mechanism 130 may have a substantially circular cross-section with a diameter of 10 millimeters (mm), as shown in FIG. 2.

Figure 5:
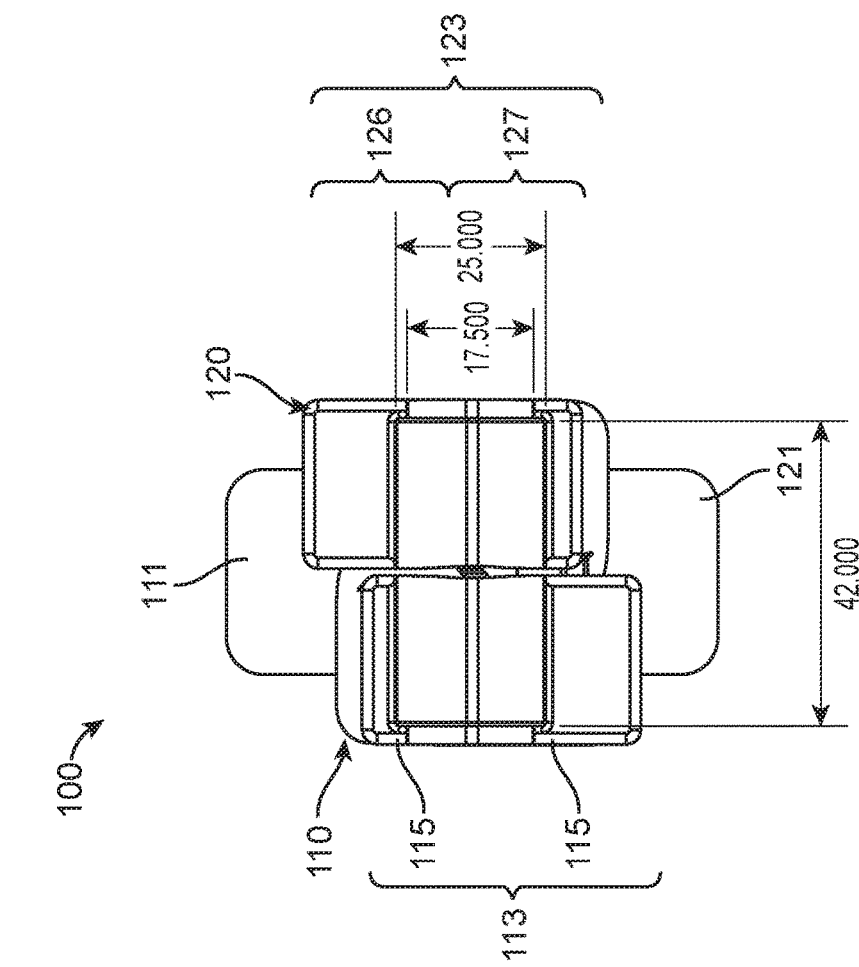
FIG. 5 is a side view at the distal end of the clip separation tool of FIG. 1, according to one example embodiment.
Figure 4:
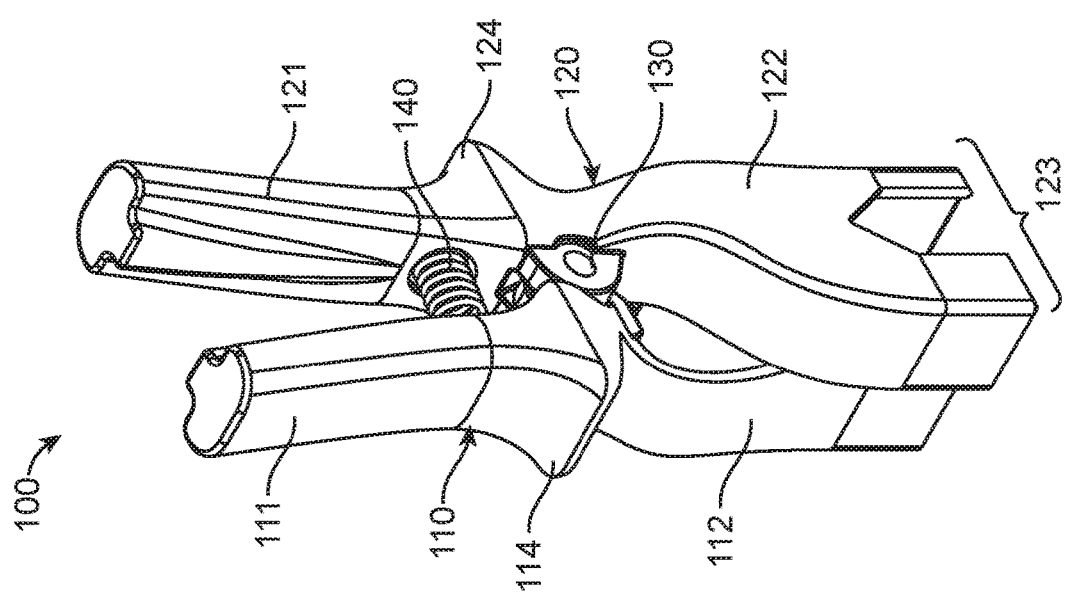
FIG. 4 is a perspective view at a proximal end of the clip separation tool of FIG. 1, according to one example embodiment.
Figure 6:
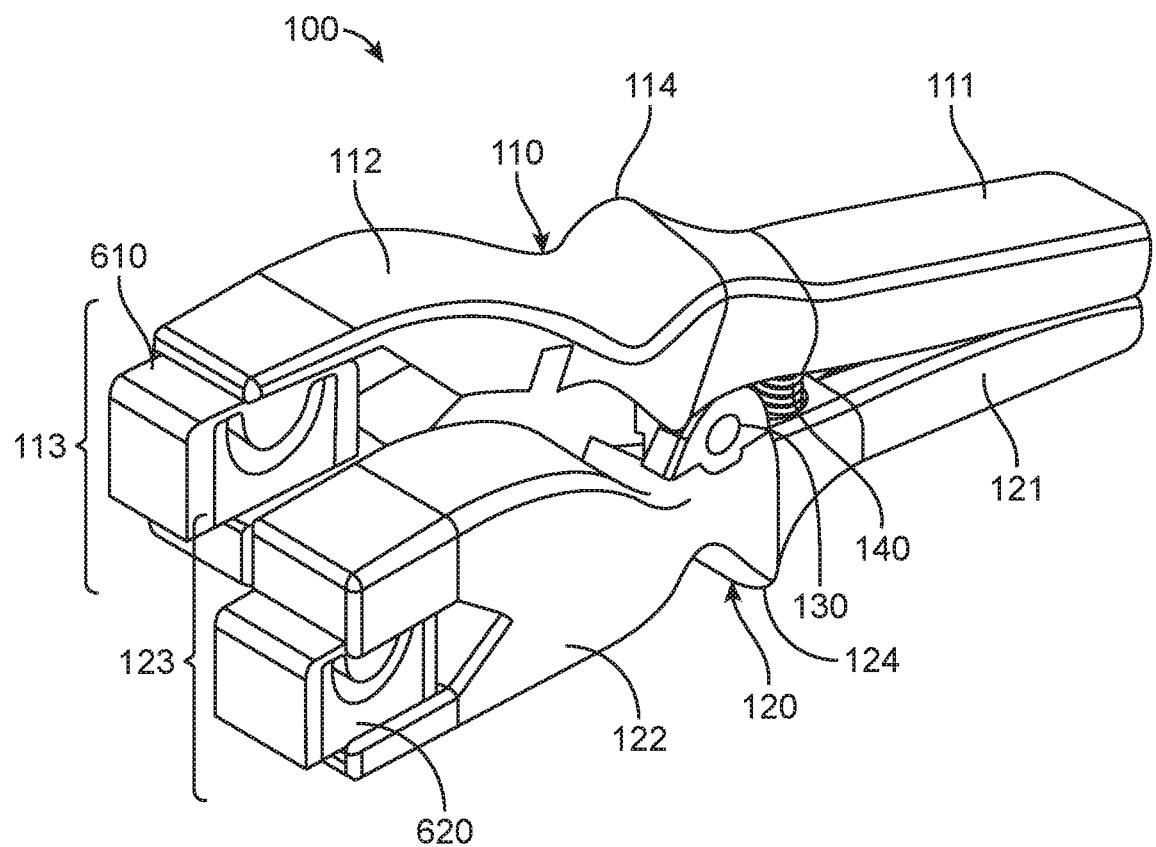
FIG. 6 is a perspective view at the distal end of the clip separation tool in an engaged position, according to one example embodiment.

The spring 140 biases the arms 110 and 120 to rotate to or maintain the equilibrium position as shown in FIGS. 1-5. The spring is compressible such that the clip separation tool 100 may achieve an engaged position, as shown in FIG. 6. The motion and operation of the clip separation tool 100 to achieve this engaged position and return to the equilibrium position is described in further detail in the description of FIG. 6. Alternatively, the spring 140 may be any spring mechanism for receiving a force to compress from an equilibrium position and return to the steady state position upon release of the force (e.g., a gas spring). In some embodiments, the interior surface of at least one of the proximal ends 111 and 121 includes a cavity for receiving the spring 140 such that the motion of the spring 140 is limited to only the direction in which it compresses and expands.

Figure 3:
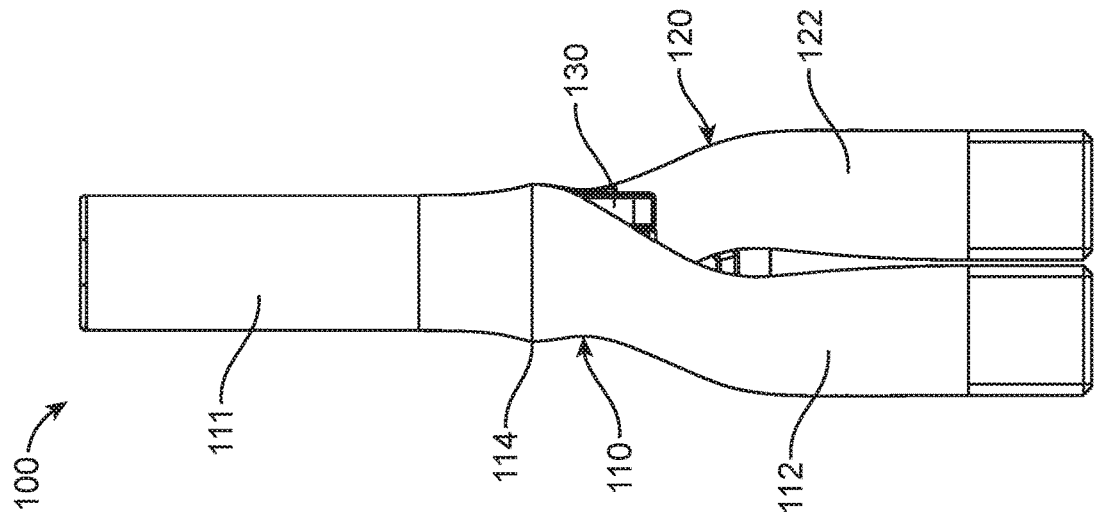
FIG. 3 is a top view of the clip separation tool of FIG. 1, according to one example embodiment.

The clip separation tool 100 may be sized to be used manually. In some embodiments, the clip separation tool 100 is approximately 179 mm in length, 63.655 mm in height, and approximately 42 mm wide. The length of the proximal end of the clip separation tool 100 may be between 50-200 mm long. To reduce the likelihood that the separation force exerted upon the clips rotates the clips during separation, the jaws may be placed further from the pivot mechanism 130. In some embodiments, length of the distal end may be between 30-150 mm. As the length of the distal end increases, the lever force required by the user to separate the clips using the tool decreases. The tool width may be determined based on a tradeoff between ergonomic and mechanical integrity: as the width narrows, the operability of the tool under the force applied by a user's arm decreases and as the width increases, using the tool becomes increasingly cumbersome and uncomfortable. The distal end of the clip separation tool 100 may have a greater width than the width of the proximal end. For example, the proximal ends 111 and 121 overlap one another while the distal ends 112 and 122 do not, as shown in FIG. 3, contributing to the width difference. A handle portion at the proximal end may be approximately 60 mm long. While the distal and proximal ends 112 and 111 are each approximately 50% of the arm 110, an arm may be partitioned into a distal end and proximal end in other ratios. For example, the proximal ends 111 and 121 may be 60% of the lengths of the arms 110 and 120.

Each of the pairs of jaws 113 and 123 includes a top jaw and a bottom jaw. In one embodiment, the top jaw is larger than the bottom jaw. For example, the pair of jaws 123 includes the top jaw 126 and the bottom jaw 127. The top jaw 126 is larger to encourage the disconnect of the clips, where the force applied to the clip within the pair of jaws 123 is applied substantially from the top jaw 126 to the clip. As shown in FIG. 5, the top jaws may have a height of 14.012 mm and the bottom jaws may have a height of 6.488 mm. The clip separation tool 100 may be sized for clips that are used with tubing having a range of inner radii (e.g., from 3.175 to 12.7 mm) and outer radii (e.g., from 6.35 to 19.05 mm).

The dimensions of the jaw openings are sized to account for the dimensions of an engaged sterile line clip, whose height can be smaller than the diameter of the tubing. For example, the widths and heights of the openings of each of the jaws 113 and 123 may be 21 mm and 17.5 mm, respectively. The clip separation tool 100 receives and maintains clips within the jaws 113 and 123 with enough resistance such that the clips can be both secured within its jaws after the clips are disconnected from one another and removed from the jaw with minimal force. In some embodiments, the clip separation tool 100 may engage with clips of different sizes. The clip separation tool 100 may include jaw attachments, swappable jaws, or an adjustable jaw (e.g., using a worm gear). As shown in FIGS. 1 and 5, one or more edges of each of the jaws 113 and 123 are raised to receive and maintain a clip within the jaw. For example, the raised edges 115 have a height of approximately 1.5 mm.

Material from which the clip separation tool 100 may be manufactured includes nylon, reinforced nylon (e.g., a carbon fiber and nylon blend), carbon fiber, metal, glass fiber, any comparable material with a flexural modulus between 1.5-450 gigapascals (GPa) and notched Izod impact strength of at least 20 joules per meter (J/m), or a suitable combination thereof. Additionally, the tool may be fabricated using a non-additive manufacturing technique such as injection molding or machining. The spring 140 may be separately manufactured from the clip separation tool 100 and may be manufactured from a metal or plastic having elastic properties. Different parts of the clip separation tool 100 may be manufactured using different materials. For example, the handle portions may be manufactured using silicone or other suitable material for improved grip during use while the remainder of the arms 110 and 120 are manufactured using reinforced nylon and glass fiber. The material or materials used may be selected based on the requirements of a classified environment in which it may be used. A method of manufacturing the clip separation tool 100 is described in the description of FIG. 8.

In some embodiments, the clip separation tool 100 is structured to be ergonomic for repeated use by a hand. The protrusion 114, 124 along the outer surface of the proximal ends 111 and 121 is structured to align with a curvature of a finger pad to promote an ergonomic fit of the tool within the hand. The shape of the clip separation tool 100 may, as shown in the side view in FIG. 2, be helix-like with a curved inner and outer surface. The curved surface may be smooth (e.g., no ridges or sharp corners) to allow for thorough cleaning of the tool's surfaces.

Clip Separation Tool Operation

The clip separation tool described herein can be used to disconnect sterile line clips from tubing. The clip separation tool 100 of FIG. 1 is shown in an equilibrium stage prior to engagement with sterile line clips 610 and 620. During operation, a user handles the clip separation tool 100 at handle portions of the proximal ends 111 and 121 of the tool. The distal ends 112 and 122 of the tool 100 receive connected line clips within jaws 113 and 123. The user may then apply force to the handle portions to engage the clip separation tool 100, disconnecting the sterile line clips 610 and 620.

FIG. 6 shows the clip separation tool 100 in an engaged position during operational use. Prior to reaching this position, the jaws of the arms are substantially aligned to receive the connected clips. In particular, the top surface of the jaw 113 of the first arm 110 is aligned with the top surface of the jaw 123 of the second arm 120 such that the top surfaces are within the same plane. Likewise, the bottom surface of the jaw 113 of the first arm 110 is aligned with the bottom surface of the jaw 123 of the second arm 120 such that the bottom surfaces are within the same plane.

After receiving the connected clips, the pairs of jaws cooperate to disconnect the clips from one another responsive to a force being applied to the handle portions at the proximal ends 111 and 121 of the arms. This cooperation to disconnect the clips involves the arms 110 and 120 rotating relative to each other around the pivot mechanism 130 responsive to the force being applied. As the force is applied to the handle portions of the arms 110 and 120, the distal ends 112 and 122 rotate or pivot away from one another and the proximal ends 111 and 121 pivot towards one another. The pivot of the distal ends 112 and 122 away from one another provide force to disconnect connected clips 610 and 620 within the jaws 113 and 123.

In some embodiments, the force is applied from a user's hand operating the clip separation tool 100. For example, a user may operate the tool with one hand and hold the tubing in the other hand while applying force to disconnect the sterile line clips. The configuration of the clip separation tool 100 to be used single-handedly allows the user to simultaneously remove the disconnected clips 610 and 620 from the jaws 113 and 123 with one hand and hold the clip separation tool 100 with the other hand. Alternatively, the force may be from a mechanical system of which the clip separation tool 100 is integrated into as a component so that a force from the mechanical system operates the clip separation tool 100.

In some embodiments, the tool is configured for use in an ISO 7 environment. For example, to be compliant with the sanitary requirement defined by the ISO 7 standard, the clip separation tool 100's surfaces may be smooth, avoiding ridges or any other surface definition that are not easily sanitized through a wipe of the surface.

Figure 7:
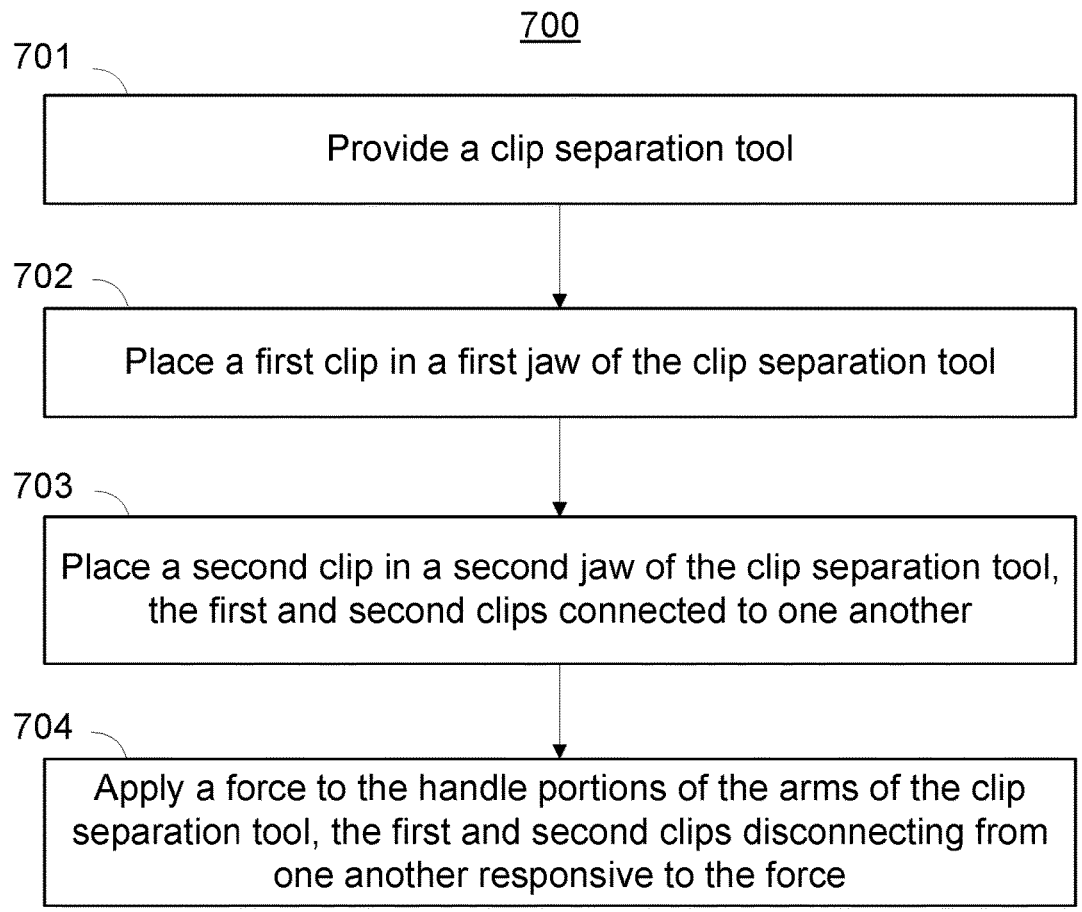
FIG. 7 is a flowchart illustrating a process for using a clip separation tool, according to one example embodiment.

FIG. 7 is a flowchart illustrating a process 700 for using a clip separation tool, according to one example embodiment. A pair of clips are connected during the process of severing tubing. Although the connected clips could be separated via a user's hands, the amount of force needed may present ergonomic challenges because the clips have been securely connected to one another to prevent the contents of the tubing from escaping while the tubing is severed. By following the process 700, the user can follow a more ergonomic practice to separate the clips from one another. The process 700 begins with providing 701 a clip separation tool as described herein for use. To begin disconnecting a connected pair of clips, the connected pair of clips is first placed within the clip separation tool. For example, the clip 610 of the connected clips 610 and 620 is placed 702 in the first pair of jaws 113 and the clip 620 is placed 703 in the second pair of jaws 123. The pairs of jaws 113 and 123 may engage with the clips 610 and 620 at the same time or at substantially the same time because the clips are still connected when inserted into the jaws. To disconnect the connected pair of clips, a force is applied 704 to the handle portions of the arms of the clip separation tool, the force causing the arms of the tool to rotate around the pivot mechanism of the tool such that the distal ends of the arms pivot away from one another and the connected clips disconnect. That is, applying 704 a force to the handle portions of the proximal ends 111 and 121 of the clip separation tool 100 causes the distal ends 112 and 122 to pivot away from one another and disconnect the clips 610 and 620 from one another.

Clip Separation Tool Manufacture

Figure 8:
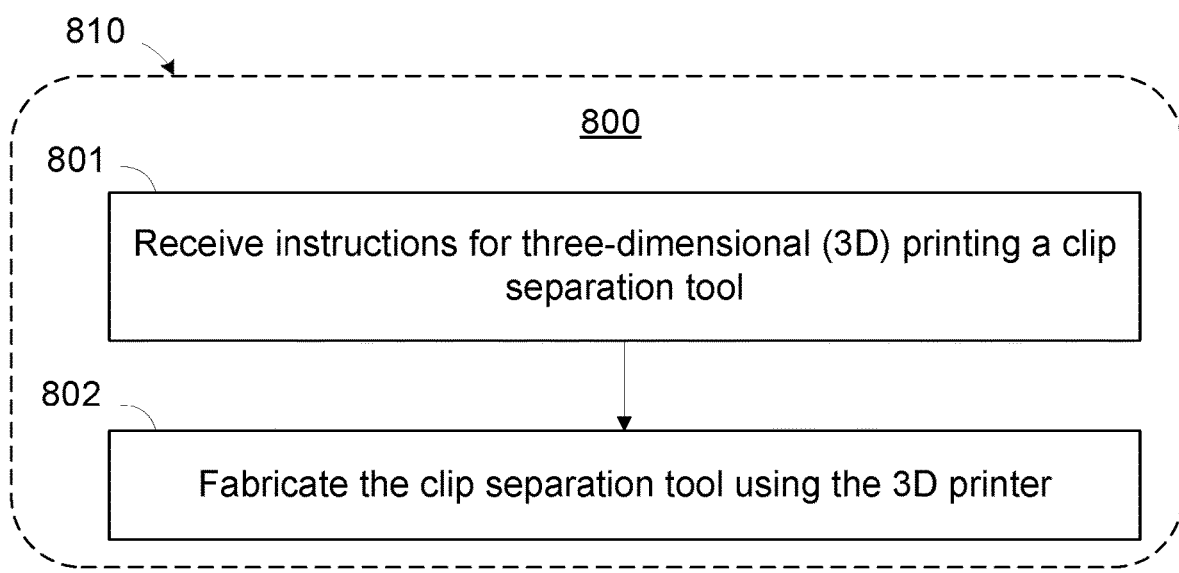
FIG. 8 is a flowchart illustrating a process for manufacturing a clip separation tool, according to one example embodiment.

FIG. 8 is a flowchart illustrating a process 800 for manufacturing a clip separation tool, according to one example embodiment. In one embodiment, a non-transitory computer readable medium 810 stores instructions that, when executed by one or more processors of a system, cause the system to perform the method 800. Thus, the system is enabled to receive 801 instructions for 3D printing a clip separation tool as described herein and fabricate 802 the clip separation tool using a 3D printer. The tool may be fabricated using any suitable additive manufacturing technique. For example, an additive manufacturing system having one or more processors may receive instructions from a non-transitory computer readable medium for manufacturing the tool using one or more additive manufacturing techniques and execute those instructions to manufacture the tool. Additionally, the tool may be fabricated using a non-additive manufacturing technique such as injection molding or machining that involves a machine whose operations may be realized upon the execution of instructions stored on non-transitory computer readable medium 810.

Additional Considerations

The clip separation tool described herein may increase the efficiency of the overall process for severing tubing and specifically, the process for separating connected clips used when severing the tubes. This is due at least in part to the clip separation tool being able to disconnect clips at speeds that are orders of magnitude faster than manual disconnection. In one example, a particular manufacturer's sterile line clips could take up to six minutes to disconnect without a tool, where a user directly engages the clips with his hands to disconnect them. In contrast, the clip separation tool may disconnect that manufacturer's sterile line clips within seconds (e.g., approximately 5 seconds).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Where values are described as "approximate" or "substantially" (or their derivatives), such values should be construed as accurate +/−10% unless another meaning is apparent from the context. From example, "approximately ten" should be understood to mean "in a range from nine to eleven."

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A tool comprising:
    first and second arms, each arm including:
        a proximal end comprising a handle portion, and
        a distal end, opposite the proximal end, comprising a pair of jaws, each pair of jaws including a top jaw and a bottom jaw, the top jaw including an inner surface configured to engage with a top external surface of a corresponding tubing attachment of a pair of connected tubing attachments, and the bottom jaw including an inner surface, disposed opposite to and facing the inner surface of the top jaw, configured to engage with a bottom external surface of the corresponding tubing attachment of the pair of connected tubing attachments, wherein the inner surface of the top jaw and the inner surface of the bottom jaw are configured to have an invariant spatial relationship relative to each other while a force is applied to the handle portions of the first and second arms;
    a pivot mechanism that rotationally couples the arms such that, responsive to the force applied to the handle portions of the arms, the arms are configured to rotate relative to each other around the pivot mechanism in a rotational plane causing the distal ends of the arms pivot away from one another and the proximal ends of the arms pivot towards one another, wherein the pairs of jaws of the first and second arms cooperate to disconnect the pair of connected tubing attachments and slide the pair of disconnected tubing attachments past each other responsive to the force being applied to the handle portions of the arms; and
    a spring biasing the arms to rotate to an equilibrium position in which the pairs of jaws are substantially aligned, the inner surface of the top jaw of the first pair of jaws is aligned with the inner surface of the bottom jaw of the second pair of jaws and an outer surface of the top jaw of the first pair of jaws is unaligned with an outer surface of the bottom jaw of the second pair of jaws, wherein the equilibrium position is attained automatically under spring loading once the proximal ends of arms are relieved of loading.

2. The tool of claim 1, wherein the pivot mechanism includes an axle and a plurality of fastening elements configured to restrict the movement of the arms to movement within the rotational plane, the arms configured to rotate around the axle.

3. The tool of claim 1, wherein the proximal end of the first arm overlaps with the proximal end of the second arm such that a width of the distal end of the tool is larger than a width of the proximal end of the tool.

4. The tool of claim 1, wherein the tool is configured to be actuated by one hand of a user.

5. The tool of claim 1, wherein each of the jaws are adjustable to engage with each of the pair of connected tubing attachments; wherein the pair of connected tubing attachments comprises a plurality of tubing attachment sizes.

6. The tool of claim 1, wherein the tool is composed of a material comprising at least one of nylon, reinforced nylon, carbon fiber, metal, or glass fiber.

7. The tool of claim 1, wherein outer surfaces of the proximal ends of the arms include respective protrusions structured to align with a curvature of a finger pad.

8. The tool of claim 1, wherein the tool was fabricated using 3D printing.

9. The tool of claim 1, wherein at least one of the first arm or the second arm is manufactured as a single piece.

10. The tool of claim 1, wherein the first arm and the second arm have identical structure.

* * * * *